United States Patent [19]

Stewart et al.

[11] Patent Number: 4,721,113

[45] Date of Patent: Jan. 26, 1988

[54] METHOD OF PREDICTING THE OCCURRENCE OF DEEP VEIN THROMBOSIS BY NON-INVASIVE MEASUREMENT OF VESSEL DIAMETER

[75] Inventors: Gwendolyn J. Stewart, Bala Cynwyd; Marvin C. Ziskin, Philadelphia; Charles M. Philips, Philadelphia; Philip D. Alburger, Philadelphia; John W. Lachman, Philadelphia; all of Pa.

[73] Assignee: Temple University of the Commonwealth System of Higher Education, Philadelphia, Pa.

[21] Appl. No.: 778,589

[22] Filed: Sep. 20, 1985

[51] Int. Cl.⁴ .............................................. A61B 10/00
[52] U.S. Cl. .................................... 128/661; 128/668; 128/134
[58] Field of Search ............... 128/660, 663, 133, 134, 128/630, 668, 694; 73/612, 861.25

[56] References Cited

U.S. PATENT DOCUMENTS

| | | | |
|---|---|---|---|
| 3,554,030 | 1/1971 | Peronneau | 128/663 |
| 4,095,597 | 6/1978 | Hassler | 128/663 |
| 4,261,367 | 4/1981 | Freese | 128/660 |
| 4,359,055 | 11/1982 | Carlson | 128/660 |
| 4,370,985 | 2/1983 | Takeichi et al. | 128/663 |
| 4,397,194 | 8/1983 | Soltz | 73/227 |
| 4,407,277 | 10/1983 | Ellison | 128/133 |
| 4,508,121 | 4/1985 | Myers | 128/660 |
| 4,526,165 | 7/1985 | Mielnik et al. | 128/133 |
| 4,546,773 | 10/1985 | Kremer et al. | 128/660 |
| 4,564,018 | 1/1986 | Hutchison et al. | 128/660 |

OTHER PUBLICATIONS

Devaney et al, "Continuous Measurement of Vascular Diameters via Television Microscopy", Proceedings of the 12th Annual Rocky Mountain Bioengineering Symposium and the 12th International ISA Biomedical Sciences Instrumentation Symposium, Denver, Colo., USA, 28-30, Apr. 1975, pp. 1-6.

Primary Examiner—Kyle L. Howell
Assistant Examiner—Ruth S. Smith
Attorney, Agent, or Firm—Seidel, Gonda, Goldhammer & Abbott

[57] ABSTRACT

A method of predicting the occurrence of deep vein thrombosis after a surgical procedure comprises monitoring changes in the internal diameter of a blood vessel using a non-invasive ultrasound technique. The frequency and magnitude of changes in vessel diameter are used to predict whether deep vein thrombosis will occur.

3 Claims, 8 Drawing Figures

METHOD OF PREDICTING THE OCCURRENCE OF DEEP VEIN THROMBOSIS BY NON-INVASIVE MEASUREMENT OF VESSEL DIAMETER

The Government of the United States of America has rights in this invention pursuant to Grant No. HHS AM 28428 awarded by the Department of Health and Human Services through the National Institute of Health (NIH).

SCOPE OF THE INVENTION

The present invention is generally directed to a method of and apparatus for obtaining a continuous recording of an internal dimension of a blood vessel or other hollow structures versus time. The continuous recording of the internal dimension of any hollow structure can be obtained non-invasively when walls of the structure are substantially but not completely transparent to ultrasonic radiation and the substance between the walls has a lesser ability to reflect ultrasonic radiation than the walls (i.e., a different acoustic impedance or an "acoustic discontinuity"). More specifically, the present invention is directed to a method of and apparatus for predicting the occurrence of post-operative deep vein thrombosis (DVT) from intraoperative changes in an internal diameter of a vein remote from the operative site.

BACKGROUND OF THE INVENTION

The use of diagnostic ultrasound to examine the interior portions of a living creature without exploratory surgery is known. Ultrasound examination is preferred over exploratory surgery for obvious reasons. Exploratory surgery requires anesthesia, cutting of tissue and exposure of a body portion. These procedures carry the inherent risk of anesthesia and also require inflicting local tissue trauma with accompanying inflamation and introducing the risk of infection. Both local tissue trauma and infection may cause secondary effects throughout the body. In contrast, ultrasound is non-invasive, so it does not require anesthesia and causes no trauma or risk of infection. Avoiding exploratory surgery with its accompanying consequences is desirable in any clinical setting and is essential if the response of blood vessels or any other tissue to specific traumatic conditions are to be measured.

The use of ultrasound to examine arteries is known. An early ultrasound instrument utilized the A-mode of display to measure the external diameter of the exposed aorta and femoral artery in an animal model. When the arteries were exposed and the crystal was placed directly over the artery, it was possible to identify the structures (walls) giving rise to the echoes displayed in the A-mode. See Hokanson, D. E., et al., *A phase locked echo tracking system for recording arterial diameter changes in vivo*, J. Appl. Physiol. 32:728-735, 1972. However, it was difficult to identify the structures from which the echoes originated without exposing the vessels because, the skin, muscle and other tissues located between a crystal from which ultrasonic radiation is generated and the artery can give rise to independent echoes of their own. For this reason the development of ultrasound equipment for use in examining blood vessels has taken a rather different direction. The equipment most frequently employed utilizes real time, B-mode, scanning (continuous gray scale). Real time means an instantaneous representation of the section being examined such that it instantly shows changes in the structure being examined. The B-mode provides a recognizible two dimensional image of structures displayed on a video screen. See generally Kremkau, *Diagnostic Ultrasound: Physical Principles and Exercises*, Grunne and Stratton, 1980. Real time B-mode ultrasound has found wide use in examination of extracranial carotid arteries for atherosclerotic lesions. Other arteries and veins have also been examined by ultrasound. In these studies real time B-mode has been used and measurement of vessel diameter has often been made from frozen images on the viewing screen. The following textbooks generally describe the principles and uses of the diagnostic ultrasound and provide a background for understanding the present invention: Goldberg, Kolter, Ziskin and Waxham, *Diagnostic Uses of Ultrasound*, Grune and Stratton, 1975; Wells, P. N. T., *Biomedical Ultrasonics*, Academic Press, 1977; McDicken, *Diagnostic Ultrasonics: Principles and Use of Instruments*, Second edition, Wiley Medical, 1981; Wells, P. N. T. and Ziskin, M. C., *New Techniques and Instrumentation in Ultrasonography*, Churchill Livingston, 1980; Sanders, R. and James. S. A., *Ultrasonography in Obstetrics and Gynecology*, Appleton-Century-Crofts, 1980; Bernstein, E. F. Editor, *Noninvasive Techniques in Vascular Disease*, C. V. Mosby Co., 1979; and Repacholi, H. and Benwell, D. A., *Essentials of Medical Ultrasound: A Practical Introduction to The Principles, Techniques and Biomedical Applications*, Humana Press, 1982.

The following publications are also illustrative of the state of the art in diagnostic ultrasonic techniques. Reference to these publications is suggested for a greater understanding of the invention: Hokanson, D. E., et al., *A Phase Locked Echo Tracking System For Recording Arterial Diameter Changes In Vivo*, Journal of Applied Physiology, Vol. 32, No. 5, May 1972, pp. 728-733; Olson, R. M., et al., *A Nondestructive Technique To Measure Wall Displacement In The Thoracio Aorta*, Journal of Applied Physiology, Vol. 32, No. 1, January 1972, pp. 147-151; Garth, K. E., et al., *Duplex Ultrasound Scanning Of the Carotoid Arteries With Velocity Spectrum Analysis*, Radiology, Vol. 147, No. 3, June 1983, pp. 823-827; Evans G. C., et al., *Echoaortography*, The American Journal of Cardiology, Vol. 19, January 1967, pp. 91-96; James, E. M., et al., *High Resolution Dynamic Ultrasound Imaging Of The Carotid Bifurcation: A Prospective Evaluation*, Radiology, Vol. 144, September 1982, pp. 853-858; and Comerota, A. J., et al., *Real-Time B-Mode Carotid Imaging In Diagnosis of Cerebrovascular Disease*, Surgery, Vol. 89, No. 6, June 1981, pp. 718-729.

In general, real time ultrasound provides a means of studying the response of blood vessels in situ without surgically exposing the vessel. This is important for two reasons. First, vascoactive substances released or synthesized in response to the surgery required to expose the vessel may very well induce constriction or dilation of the vessel. These changes in vessel diameter make it impossible to obtain true data on the response of the vessel to experimental factors. Second, surgical exposure of a blood vessel in the human patient is not acceptable, so a non-invasive method is required for any human study. Angiography cannot be used for prolonged or repeated measurements and in addition the radiopaque material may cause a change in vessel diameter immediately.

SUMMARY OF THE INVENTION

In a structure such as a fluid conducting vessel having substantially but not completely ultrasound transparent anterior and posterior walls and an acoustic discontinuity therebetween, a method for non-invasively monitoring changes in the internal diameter of the structure comprises the steps of:

generating an incident ultrasound pulse and directing the incident pulse toward the anterior and posterior walls of the structure;

receiving echoes indicative of the presence of each of the anterior and posterior walls of the structure and caused by the acoustic discontinuity therebetween, wherein each echo is a reflected pulse having a leading and a trailing edge;

providing an indication of the time difference between the occurrence of the trailing edge of the echo indicative of the presence of the anterior wall and the leading edge of the echo indicative of the presence of the posterior wall, wherein the time difference is an indication of the structure's internal dimension;

repeatedly performing the aforementioned steps in a cyclic sequence; and providing a real time analog recording of the structure's dimension versus time, whereas changes in structure dimension may be monitored.

The method has particular application in monitoring the diameter of blood vessels, and particularly veins, over time, during surgery. According to the method of the present invention, dilations in vessel diameter that occur during surgery are utilized to predict the occurrence of deep vein thrombosis.

For use in cases where the structure whose dimension to be measured is embedded in a mobile body part such as a human limb, an apparatus is provided for maintaining the body part stationary with respect to the ultrasound probe during the measurement interval. According to the present invention, one such apparatus comprises a specially designed table adapted to releasably secure a probe associated with the ultrasonic generating and signal processing equipment above the body part. The table comprises an adjustable support column connecting the table top to the table base and a platform parallel to and spaced above the top. Low friction means are provided for permitting multi-directional, uniplanar movement of the platform in a plane parallel to the top.

One object of the present invention is to provide a method for determining an intra-structure dimension using a non-invasive technique.

Another object of the invention is to provide a method of predicting the occurrence of thrombosis that may occur as a result of traumatic surgery using non-invasive ultrasound techniques.

Other objects and advantages will become apparent hereinafter.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 7:
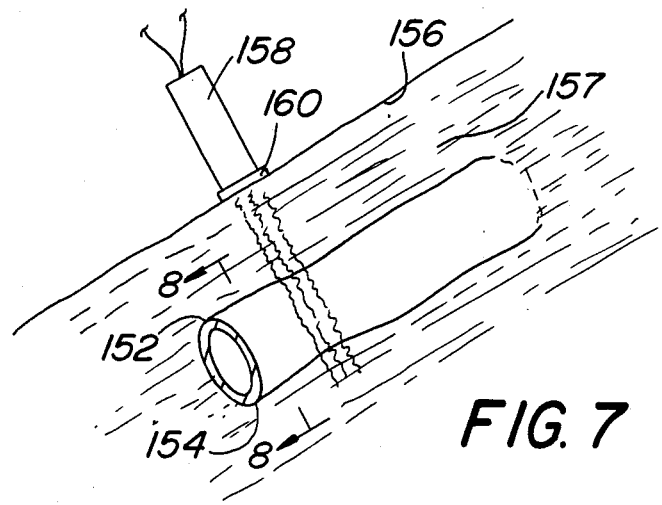
FIG. 7 illustrates a vessel whose internal diameter is to be measured as being situated beneath a surface such as skin and tissue.

Referring now to the drawings, wherein like numerals represent like elements, there is shown in FIG. 7 a vessel 150 whose internal diameter or other dimension is to be measured. (As used herein, the term vessel includes arteries, veins and any other substantially ultrasound transparent structures). As shown, vessel 150 is situated beneath a surface 156. Both vessel 150 and surface 156 are substantially ultrasound transparent. Vessel 150 may be a fluid conducting vessel such as a blood vessel buried beneath skin and tissue, as represented by numerals 156 and 157. Vessel 150 has anterior and posterior walls 152, 154 respectively, with respect to surface 156. A probe 158 associated with ultrasonic generating and processing equipment (described hereinafter) is placed over the surface 156 for the purpose of measuring the diameter or other dimension of vessel 150 according to the method disclosed herein. A transmissive gel 160 is disposed between the probe 158 and surface 156, as those skilled in the art will readily recognize is required.

Figure 8:
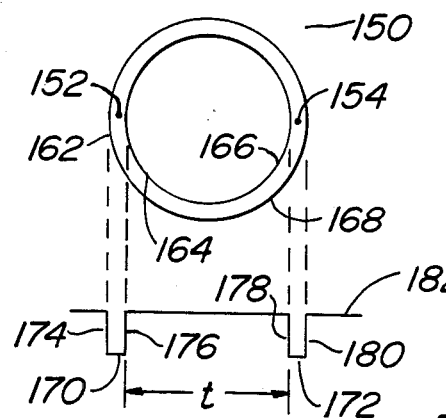
FIG. 8 is a cross sectional view taken along line 8—8 of FIG. 7 and also illustrates an A-mode display.

As best illustrated in FIG. 8, vessel 150 is generally circular in cross section and its anterior and posterior walls 152, 154 have a thickness defined by a distance between interior and exterior surfaces of the walls thereof. Anterior wall 152 has exterior surface 162 and interior surface 164. Similarly, posterior wall 154 has exterior surface 168 and interior surface 166. Walls 152, 154 must be substantially but not completely ultrasound transparent and be separated by a substance having a lower acoustic impedance than that of the walls, i.e., by fluid, etc., to successfully practice the method of the present invention. This is also known as an "acoustic discontinuity". As those skilled in the art are aware, the tissue comprising the walls of blood vessels in humans and animals are ultrasound partially transparent and are separated by an acoustic discontinuity, i.e., blood. The method of the present invention enables one to obtain a measurement indicative of the internal diameter of vessel 150, i.e., the diametrical distance between interior wall 164 and interior wall 166, non-invasively using ultrasound radiation.

As is known, a representation of the distance between first and second points can be obtained by measuring the time required for an incident ultrasonic pulse to be transmitted from the first point to the second point and reflected from the second point back to the first point. The invention utilizes an extension of this principle to measure the time difference, in A-mode display, between sequential ultrasonic pulses reflected from walls 152 and 154, respectively. The reflections (also referred to herein as echoes) arise from incident ultrasonic pulses generated by ultrasonic generating equipment (described herein) and directed toward the vessel 150 whose internal diameter is to be measured as illustrated in FIG. 7.

Referring again to FIG. 8, a graphic depiction of a typical A-mode display is shown at 182. The A-mode display comprises waveform 182 having two sequential pulses 170, 172. The pulses 170, 172 represent a pair of sequential echoes caused by an incident pulse incurring an acoustic discontinuity within vessel 150. The echo represented by pulse 170 is the reflection caused by anterior wall 152; the echo represented by pulse 172 is the reflection caused by posterior wall 154. As illustrated, each echo has a rising (leading) edge and a falling (trailing) edge. The occurrence of the falling (trailing) edge 174 of pulse 170 coincides with the reflection of the incident pulse from surface 162 and the occurrence of the rising (leading) edge 176 coincides with the reflection of the incident pulse from internal surface 164. Similarly, the occurrence of the falling (trailing) edge 178 of pulse 172 coincides with the reflection of the incident pulse from internal surface 166 and the occurrence of the rising (leading) edge 180 coincides with the reflection of the incident pulse from external surface 168. What has been described thus far is well known in the art and does not comprise any of the novelty of the present invention.

As will be appreciated from the A-mode display 182 illustrated in FIG. 8, the time difference between the occurrence of the rising edge 176 of pulse 170 and the falling edge 178 of pulse 172 provides an indication of the interior diameter of vessel 150. By monitoring changes in interior vessel diameter in real time, the occurrence of post-surgical deep vein thrombosis can be predicted. An apparatus for generating the incident pulses, processing the reflected pulses and providing such a real time display will now be disclosed.

Figure 6:
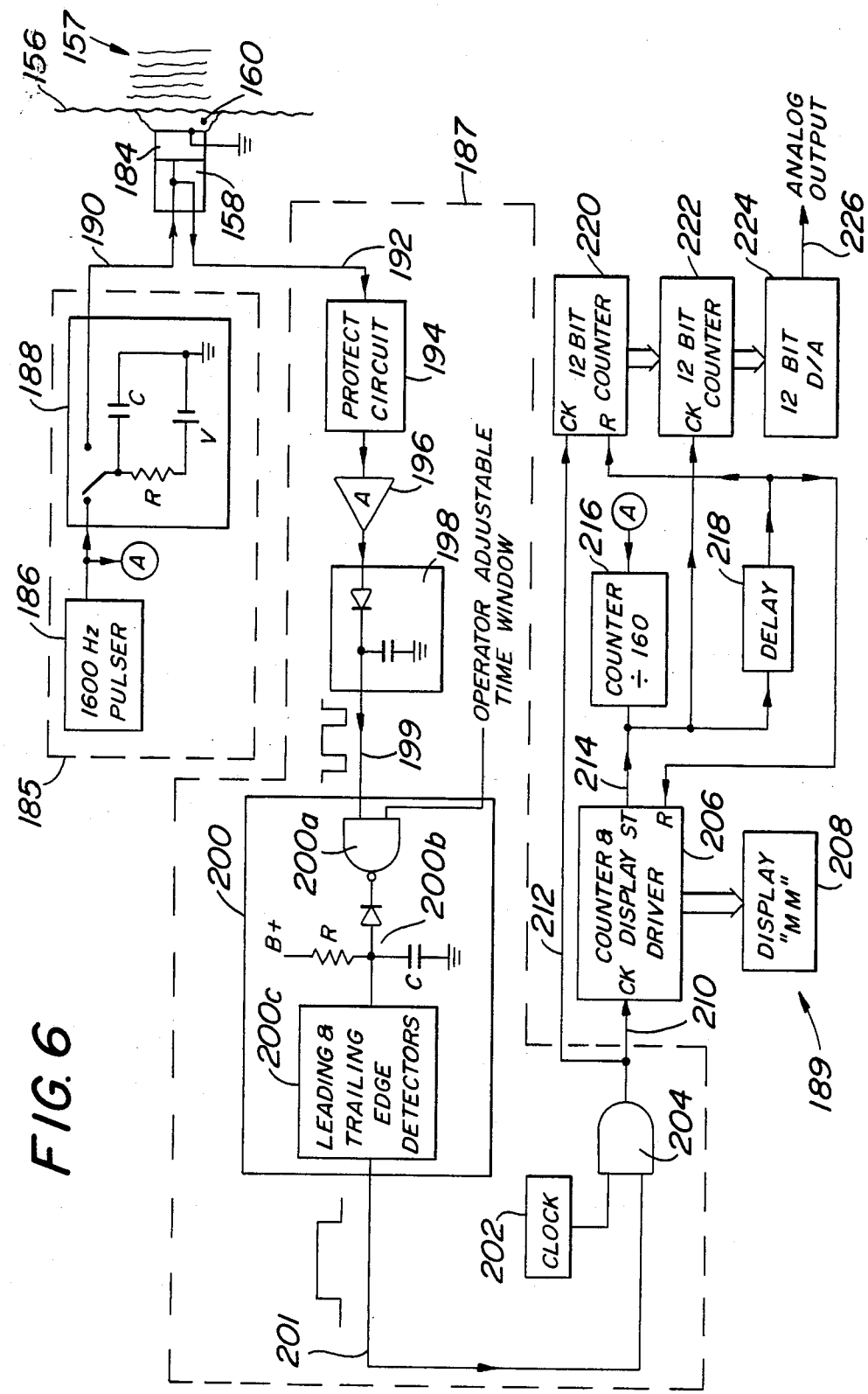
FIG. 6 is a block diagram of an A-mode ultrasound generating and receiving circuit.

An ultrasound pulse generating, echo receiving and processing instrument that may be used in connection with the practice of the present invention is commerically available from Cooper Medical Devices Corporation, 600 McCormick Street, San Leandro, Calif. 94577 and is sold under the tradename "ULTRASCAN 404". As commercially sold, such unit is adapted for ophthalomoligic measurements. Such unit is equipped with both A and B modes of display, but the A-mode display function is modified, as described herein, for use in connection with the method of the present invention. A block diagram of the circuitry of the unit, including the modifications thereto, is illustrated in FIG. 6. The B-mode display circuitry is unmodified and is utilized to locate the vessel of interest and maximize its image, as is known in the art.

Referring now to FIG. 6, the details of the electronic apparatus used in connection with the present invention will be explained.

The electronic circuit comprises an ultrasound pulse transmitter 185 for generating incident pulses, an ultrasound receiving circuit 187 for receiving ultrasound echos, and processing and display circuitry 189. Transmitter 185 comprises a pulse generating circuit 186 that generates pulses at a rate of 1600 Hz. The pulses are supplied to a power output unit 188 comprising a voltage source V and a RC charging network for generating high voltage pulses. The high voltage pulses are supplied via line 190 to a crystal 184 that rings at its resonant frequency, thereby sending ultrasonic waves through the coupling gel 160, the surface 156, anatomical tissue structure 157, toward the target vessel. As is known in the art, reflections or echos occur whenever the incident pulse incurs a medium having a different acoustic impedence or an acoustic discontinuity. This phenomenon occurs when the incident pulse incurs the anterior and posterior walls 152, 154 of vessel 150.

Crystal 184 is also used to receive the echoes and supplies them on a line 192 to a protection circuit 194. Protection circuit 194 maintains the input to the receiver 187 at safe levels during the "bang" that occurs when an incident pulse is generated. The received pulse is amplified by amplifier 196 and provided to a filter/detector 198 where it is shaped and provides output pulses on line 199 that substantially correspond to the output pulses 170, 172, as previously described. In practice, the pulses on line 199 may not be perfect, but a filter 200b is provided to "square up" these pulses for reasons herein described. The pulses on line 199 are provided to a gate 200 which provides an output pulse on line 201 having a duration corresponding to the time t between the leading (rising) and trailing (falling) edges of the sequential reflected pulses provided on line 199. See FIG. 8. The gate 200 comprises a NAND gate 200a that receives the pulses on line 199 on one input and an operator adjustable time window on another input. The output of gate 200a is provided to a filter 200b that eliminates the effect of multiple reflections that may cause variable triggering. The output of filter 200b is supplied to leading and trailing edge detectors 200c that generate the pulse appearing on line 201. The addition of circuitry 200c represents the basic modification to the commerically available unit hereinbefore described. As sold, such unit contains only leading edge detectors and would not provide an indication of internal vessel diameter. As is apparent, the duration of the pulse on line 201 is an indication of the internal diameter of vessel 150, i.e., the distance between the interior surface 164 and interior surface 166.

The output of circuit 200 is supplied to one input of an AND gate 204. The other input of gate 204 receives pulses from a clock 202. The frequency of clock 202 is scaled to, in effect, convert the time duration of the pulse on line 201 to a direct measurement (in millimeters) of internal vessel diameter Thus, the output of gate 204 is a series of pulse bursts wherein each pulse burst has a number of pulses representative of vessel diameter. The pulses are supplied via a line 210 to the clock input of a counter and display driver circuit 206. Circuit 206 counts the number of pulses present in each ten consecutive pulse bursts. A counter 216 receives pulses from the 1600 Hz pulser 186 and provides an indication via line 214 to the STORE input of circuit 206 that ten such pulse bursts have occurred. At that time, circuit 206 averages the readings represented by the ten pulse bursts and converts this average to seven segment display data that is supplied to display 208. Display 208 provides a display of vessel diameter in millimeters.

The pulse bursts present at the output of gate 204 are also supplied via a line 212 to the clock input of a 12 bit counter 220. As before, 12 bit counter 220 counts the number of pulses present in ten consecutive pulse bursts. The output of counter 216 is operatively connected to the clock input of a 12 bit latch 222 that receives and stores the binary output of counter 220. The data stored in the latch 222 is supplied to a 12 bit digital to analog converter 224. A real time analog signal representing internal vessel diameter is provided on line 226. The signal on line 226 may be provided to a chart recorder for providing a hard copy indication of vessel diameter versus time, whereas changes in internal vessel diameter may be monitored.

The output of counter 216 is also used to reset the counter circuits 206 and 220 by means of a delay circuit 218. The delay circuit 218 provides reset pulses to the RESET inputs of circuits 206 and 220.

As will be appreciated, some means must be provided for maintaining the vein and the probe 158 in the same relative position during the measurement period. This is necessary even when passive movement of the limb will be unavoidable during the measurement period, for example during operation. FIGS. 1 through 5 illustrate one such means.

A support table 10 generally comprises a top 12, a base 14, an adjustable column 16 and a platform 18. Adjustable column 16 stands perpendicularly on and is affixed to base 14. Base 14 is generally parallel to a floor F. Castors 30 are affixed to base 14 for rolling engagement with floor F. Castors 30 are provided with locks (now shown) to prevent rolling movement. The top 12 is affixed to an end of column 16 away from base 14. Top 12 is disposed perpendicularly to column 16 and is generally parallel to base 14.

Adjustable column 16 is adapted for raising and lowering top 12. Column 16 includes a pump 24 integral with column 16. Pump 24 has a handle 26. Handle 26 is provided to actuate the pump 24, whereby the top 12 may be raised. Pump 24 has a pressure relief valve 28. The valve 28 is integral with pump 24. Valve 28 is adapted for releasing pressure in the pump, whereby the top 12 may be lowered. Pump 24 is preferably a pneumatic pump but any pump or threaded screw device will suffice. Additionally, an automatic pump may also be used.

Figure 2:
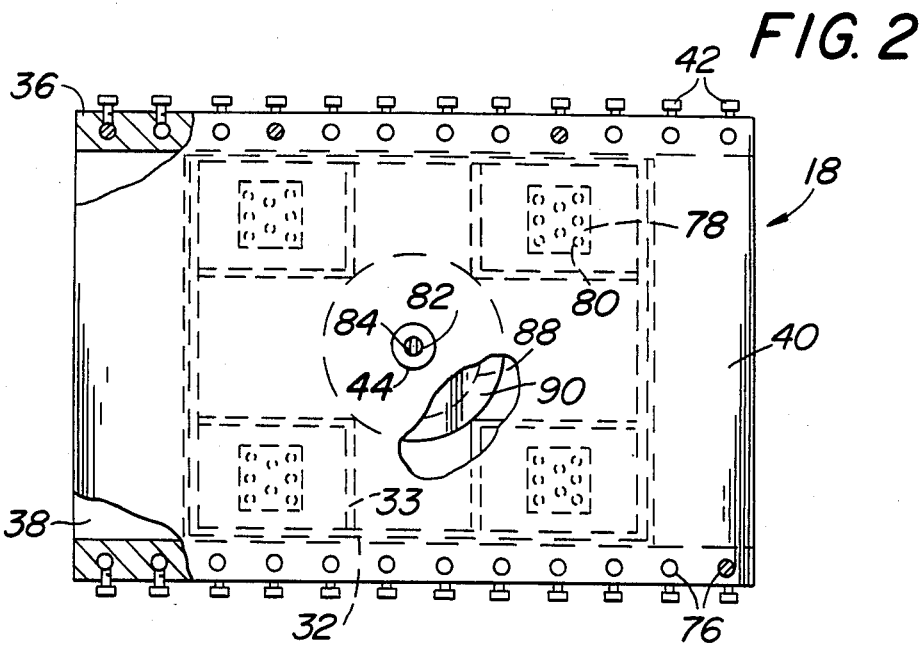
FIG. 2 is a top plan view of the support table taken along line 2—2 of FIG. 1, parts being broken away for clarity.

Referring to FIG. 2, top 12 is shown in shadow lines. Top 12 is generally rectangular. On an upper surface of top 12, bar 32 is affixed along the peripheral edge portion of top 12. In each corner portion of top 12, a compartment is defined by bars 32 and bars 33. Bar 33 is affixed to the upper surface of top 12 and is generally L-shaped. Bars 32 and 33 bound the rectangular compartment.

Within each compartment is placed a ball bearing matrix. The ball bearing matrix comprises a rectangular plate 78 having a plurality of holes 80 disposed therethrough. A ball bearing 34 is freely rotatable in each hole 80. Ball bearings 34 are of sufficient diameter to extend above bars 32 and 33 when in contact with the upper surface of top 12.

Figure 4:
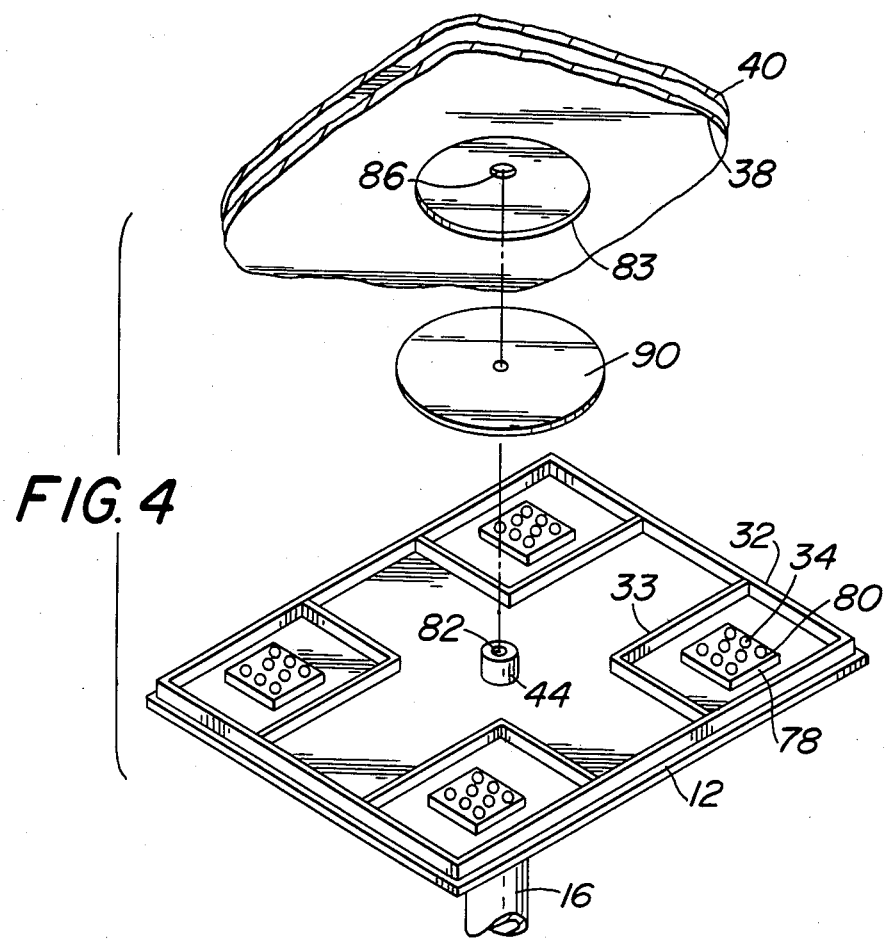
FIG. 4 is an exploded view of the support table.

Referring to FIG. 4, there is shown a cylindrical rod 44, having an aperture 82. Rod 44 is affixed along the upper surface of top 12. Rod 44 is located at the center of top 12. Rod 44 is affixed to top 12 standing on its flat surface. Aperture 82, which is coaxial with rod 44, is provided with internal threads.

Platform 18 is shown in FIGS. 2 and 4. Platform 18 generally comprises a bottom piece 38, a top piece 40 and spacers 36. Platform 18 is generally rectangular having dimensions greater than top 12.

Top piece 40 has an opening 86 which is generally circular and located at the center of top piece 40. Slots 76 are disposed along the longer edge portion of rectangular top piece 40. Slots 76 are equally spaced from one another and have equal diameters.

Bottom piece 38 is generally rectangular having the same dimensions as top piece 40. Bottom piece 38 has a second opening 88 which is generally circular and has a diameter greater than the diameter of opening 86 in top piece 40. Second opening 88 is coaxial with opening 86.

Spacers 36 are affixed between top piece 40 and bottom piece 38 along the lengthwise edge portions of platform 18 and adjacent slots 76. Slots 76 extend partially through spacer 36. Set screws 42 are provided with each slot 76. Screws 42 are located along the spacer 36 and extend outwardly therefrom. The slots 76 in each corner of the platform 18 extend completely through top piece 40, spacer 36 and bottom piece 38. Top piece 40 and bottom piece 38 are generally parallel and spaced apart from one another. Platform 18 is preferably made of aluminum.

Platform 18 rests on ball bearings 34. Ball bearings 34 allow platform 18 to be freely moved in a multi-directional uniplanar manner. A retainer disk 90 is disposed between top piece 40 and bottom piece 38. Retainer disk 90 is generally circular and has a diameter greater than the diameter of second opening 88 of bottom piece 38. Retainer disk 90 is provided with a hole through its center. Retainer disk 90 is engageable with rod 44 by a screw 84 insertable through the hole of retainer disk 90 and into threaded aperture 82. See FIG. 3. Retainer disk 90 is adapted for limiting the movement of platform 18.

Shelf 22 is a generally rectangular plate and made of aluminum. Shelf 22 is parallel to and spaced above platform 18. See FIGS. 1 and 3. Posts 46 are inserted into slots 76 of platform 18. Posts 46 are upstanding from and perpendicular to platform 18. Posts 46 are secured within slots 76 by set screws 42. Shelf 22 is provided with brackets 58. Posts 46 carry shelf 22 by means of brackets 58. Posts 46 extend through brackets 58 and shelf 22.

An impression casting 60 is shown resting on shelf 22. Impression casting 60 is provided for securing an appendage 64 of the subject to the support table 10. Additionally, impression casting 60 may rest directly on platform 18. Impression casting 60 is provided with clamps (not shown) so as to fix the placement of impression casting 60 on shelf 22 or platform 18. Shelf 22 and posts 46 are optional and their use may depend on the position of the patient during surgery.

Figure 1:
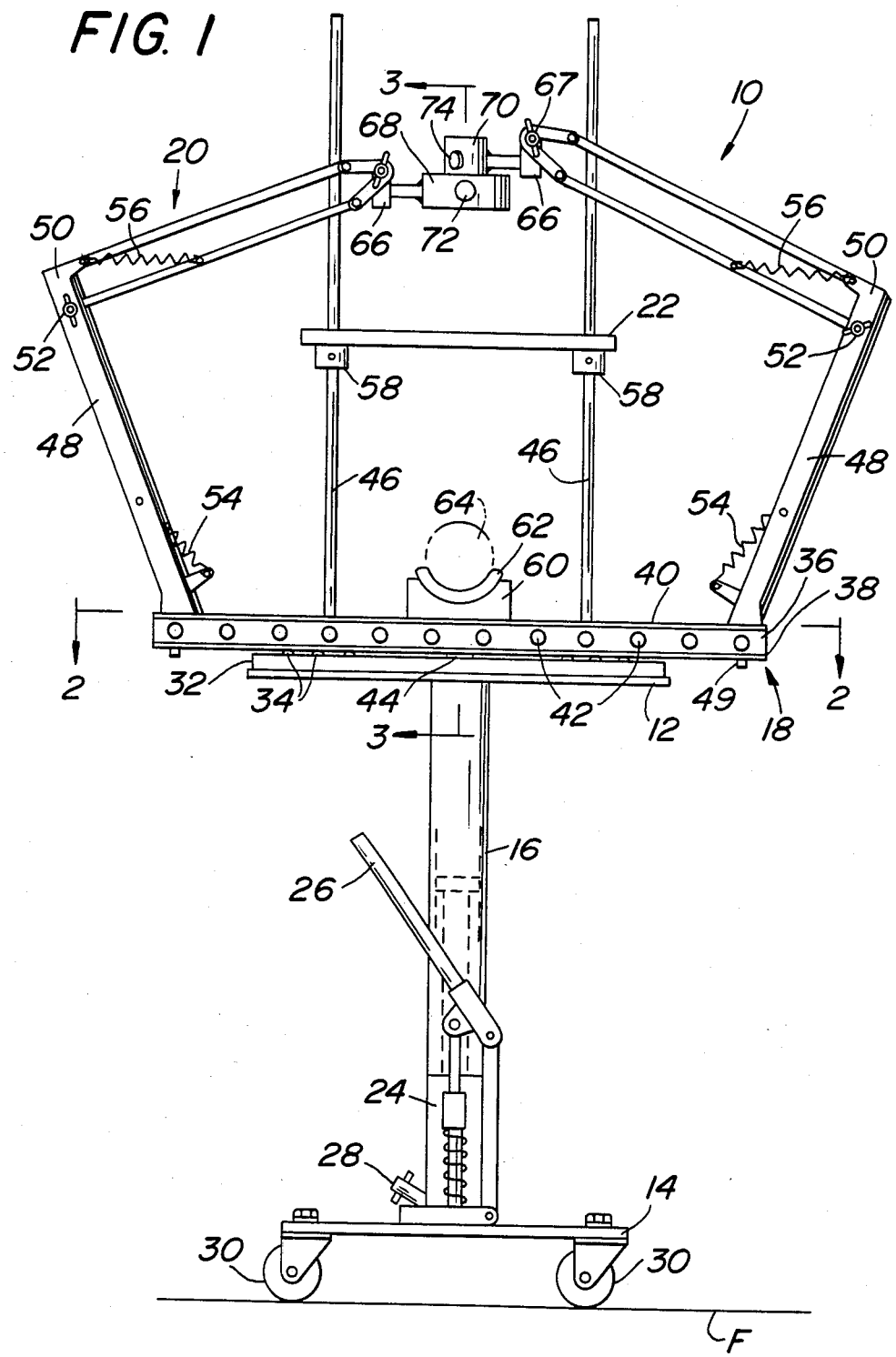
FIG. 1 is an elevational view of a support table.
Figure 3:
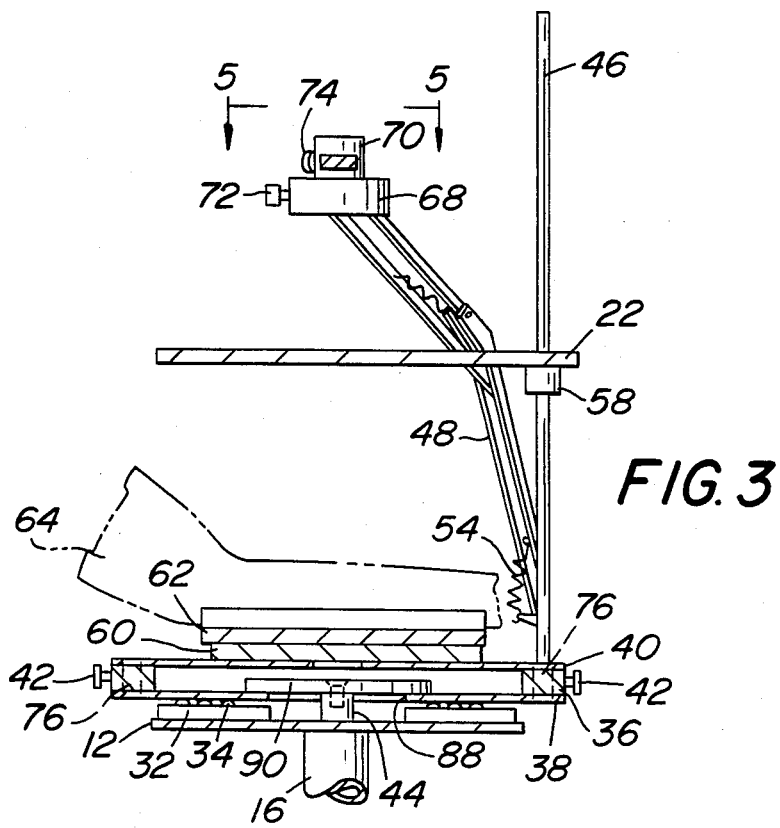
FIG. 3 is a sectional side view of a support table.

In FIGS. 1 and 3, there is shown a probe holder generally designated as 20 for holding an ultrasonic probe such as probe 158. Probe holder 20 generally comprises arms 48, joints 50, springs 54 and 56, support blocks 66, first collar 68 and second collar 70. The lower end of arm 48 is releasably movably secured to platform 18 via arm pin 49. Arm pin 49 is inserted into corner slots 76 of platform 18 and secured therein by set screw 42. The upper portion of arm 48 is connected to the lower portion of arm 48 at a joint 50. Joint 50 allows pivotable movement of the upper portion of arm 48 with respect to lower portion of arm 48. Spring 54 is provided to bias movement of the lower portion of arm 48. A spring 56 is affixed between the upper portion of the arm and the lower portion of the arm 48 and biases the upper portion of arm 48 against pivotal movement. A wingnut and bolt 52 is disposed adjacent to the joint 50, whereby the upper portion of arm 48 may be secured from movement.

At the terminal end of the upper portion of arm 48 is a support block 66. Support block 66 is pivotable or tiltable about the terminal end of the second portion of arm 48 and may be locked into position by wingnut and bolt 67.

Figure 5:
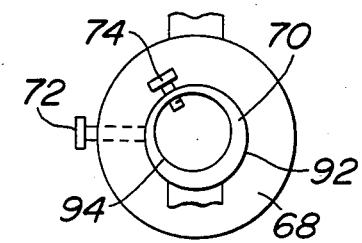
FIG. 5 is a sectional view of a probe holder taken along line 5—5 of FIG. 3.

The probe holder 20 is provided with two identical arms 48. The first arm having a support block 66 which is affixed to a first collar 68. The second arm 48 having a support block 66 which is affixed to a second collar 70. See FIG. 1. Referring to FIG. 5, first collar 68 is circular having a first bore 92 therethrough. First bore 92 is generally coaxial with collar 68 and has a set screw 72. Second collar 70 is disposed for rotational and coaxial sliding movement within first bore 92. Second collar 70 has a second bore 94 which is eccentrically disposed through collar 70. The probe may be rotated and coaxially slide within the second bore 94 and locked into place by set screw 74. The probe holder 20 is adapted for rigidly securing the probe in any position necessary to place the probe adjacent an appendage to be examined and center the probe over a dimension of the vessel to be examined.

It is imperative that the appendage or part of the subject be immobilized prior to the beginning of the examination. To immobilize the patient's appendage, an impression casting or plaster cast may be made of the appendage prior to the examination. The impression casting or plaster cast is typically made of a dental plaster. The dental plaster is mixed in a plastic bag. When the plaster becomes slightly viscous, the bag and plaster are placed in a tray or trough. The tray is somewhat longer and wider than the appendage. The chosen appendage is on the arm on the side opposite the surgery. An undercast padding 62, such as shown in FIGS. 1 and 3, can be placed over the plastic or preferably is wrapped around the appendage. The appendage, such as 64 in FIGS. 1 and 3, is depressed onto the bag of plaster, thereby forming the impression casting. It is important that the vessel to be observed is located in an uppermost position prior to pressing the appendage onto the bag of plaster. The appendage is not removed until after the plaster has hardened. The impression casting is then secured, i.e., by clamping or the like, to either the shelf 22 if the patient is positioned on the side or directly upon the platform 18 if the patient is positioned on the back. The platform 18 glides over over ball bearings 34 to accommodate inevitable movement of the patient's arm during surgery without changing the relative position of vein and probe.

The method for performing ultrasound monitoring during surgery is described. The day prior to the operation the plaster mold of the patient's hand and arm up well above the elbow is prepared and used to immobilize the hand and arm on the following day during the operation when a cephalic vein will be monitored by ultrasound.

The ultrasound scanner and the support table are moved into the operating room and placed out of the way before the patient is brought in.

After the patient has been put to sleep with anesthesia, the table, on which the plaster mold of the patient's hand and arm is placed, is moved close to but not against the operating table.

The patient's hand and arm are loosely wrapped in undercast padding and positioned in the plaster mold.

The probe is placed in approximately the correct position over the cephalic vein of the arm opposite the side of surgery and a generous amount of coupling gel (3-5 millimeters) is applied to the skin over the vein.

The ultrasound probe is placed over the vein and the instrument switched on, to the B-mode, thus providing a true picture of the internal body area adjacent the probe, as is known in the art. The investigator then moves the probe within the coupling gel until the diameter of the vessel is located. It is of the utmost importance that the diameter of the vessel be found so that true representative information pertaining to the changes in the vessel diameter may be obtained. Examination of any chord other than the diameter will give distorted readings as to the changes in the vessel diameter. Once the vessel diameter is located, the probe holder is fixed into position by securing set screws 42, wingnut and bolt 52 and wingnut and bolt 67 and set screws 72 and 74.

A sharp B-mode image of the vein is obtained by adjusting the probe holder. This is done by loosing different sets of screws to allow movement in one or more directions. After the probe and probe holder have been adjusted so that the probe is properly placed, the equipment is placed in A-mode operation.

A strip chart recorder connected to the line 226 (FIG. 6) is turned on and notes of time, steps of surgery and other information are recorded for the duration of the operation.

The mean internal diameter of the vein just before the start of the operation is used as the baseline and changes in diameter are calculated as the percentage increase (dilation) or decrease (constriction) from this value.

Experimentation has shown that changes in internal blood vessel diameter during a surgical procedure can be used to predict whether deep vein thrombosis will occur in the subject. The results of ultrasound monitoring and its comparison with two independent tests are summarized in Tables I and II. RFUT (radioactive fibrinogen uptake) is used for indication of deep vein thrombosis and venography is used for confirmation of deep vein thrombosis. Venography is done 1-7 days after the operation and after ultrasound observations are reported. In particular, experimental results indicate that the dilations of the blood vessel are the key to predicting DVT. A method of predicting the occurence of DVT according to the invention comprises the steps of: monitoring intra-vessel diameter changes during the surgical procedure; determining the magnitude of the diameter changes; and predicting based on the magnitude of the diameter dilations, the probability of deep vein thrombosis (DVT) occuring.

Finally, based on the information gathered, it may be possible to predict whether DVT or other thrombosis will occur. If the diameter dilations are of great magnitude relative to the average diameter, the chance of a lesion forming could be increased. This would be especially true of patients who have thin or weak vessel walls.

The present invention may be embodied in other specific forms without departing from the spirit or essential attributes thereof and, accordingly, reference should be made to the appended claims, rather than to the foregoing specification, as indicating the scope of the invention.

TABLE I

ULTRASOUND MONITORING OF VENOUS DIAMETER: PATIENT SUMMARY

| PATIENT | PERCENTAGE MAXIMUM CHANGE IN DIAMETER | | *RFUT (+ or −) | "VENOGRAM" (+ or −) |
|---|---|---|---|---|
| | Constriction | Dilation | | |
| Number 9 | 45 | 2 | — | — |
| Number 18 | | 7 | — | — |
| Number 19 | | 8 | — | — |
| Number 15 | 29 | 9 | — | — |
| Number 7 | 31 | 9 | — | — |
| Number 12 | 42 | 10 | + | +, calf |

TABLE I-continued

ULTRASOUND MONITORING OF VENOUS DIAMETER: PATIENT SUMMARY

| PATIENT | PERCENTAGE MAXIMUM CHANGE IN DIAMETER | | *RFUT (+ or −) | "VENO-GRAM (+ or −) |
|---|---|---|---|---|
| | Constriction | Dilation | | |
| Number 13 | 6 | 10 | − | − |
| Number 20 | | 10 | − | − |
| Number 16 | 17 | 13 | − | − |
| Number 6 | 34 | 15 | − | − |
| Number 5 | 0 | 17 | − | − |
| Number 3 | 10 | 18 | − | − |
| Number 21 | | 22 | − | − |
| Number 2 | 10 | 24 | + | +, calf |
| Number 22 | | 24 | + | +, calf |
| Number 17 | | 25 | + | +, calf |
| Number 8 | 39 | 32 | + | +, calf |
| Number 11 | 19 | 33 | + | +, calf |
| Number 1 | 12 | 38 | + | +, calf |
| Number 14 | | 38 | + | +, calf |
| Number 10 | 20 | 56 | + | +, calf +, foot calf thigh |
| Number 4 | 0 | 57 | − | +, foot |

Total number of patients: 22.

TABLE II

ULTRASOUND MONITORING OF VENOUS DIAMETER: SUMMARY OF OBSERVATIONS

| Percent Dilation | Total Number of Patients | |
|---|---|---|
| | No DVT | With DVT |
| 2–22 | 12 | 1 |
| 24–57 | 0 | 9 |

*RFUT (radioactive fibrinogen uptake) is used to indicate the development of deep vein thrombosis.
"Venography is used as the most accurate means of confirming the presence of deep vein thrombosis.
RFUT and venography are performed by an independent who have no knowledge of the ultrasound results so their results are independent of the ultrasound observations.

We anticipatre that the "yield point" for endothelium and basement membrane will be between 20–25% dilation.

The ultrasound results are reported at the end of the operation while RFUT results will become positive if at all 1–7 days after operation. Venography is performed 24–48 hours after the RFUT becomes positive.

We claim:

1. A procedure for predicting the occurrence of deep vein thrombosis by observing intra-vessel diameter changes using non-invasive pulse generating techniques comprising the steps of:
   (a) immobilizing a part of a subject having a vein;
   (b) positioning a probe over the vein of the part of the subject;
   (c) generating an incident ultrasonic pulse and directing the incident pulse toward an anterior wall of the vein;
   (d) receiving echoes indicative of the presence of each of anterior and posterior walls of the vein and being caused by an acoustic discontinuity therebetween, each echo being a reflected pulse having a leading and a trailing edge;
   (e) providing an indication of the time difference between the occurence of the trailing edge of the echo indicative of the presence of the anterior wall and the leading edge of the echo indicative of the presence of the posterior wall, the difference being an indication of vein diameter and the vein diameter being calculated therefrom;
   (f) providing a real time analog recording of vein diameter versus time;
   (g) monitoring changes in vein diameter over time while the subject is undergoing a surgical procedure;
   (h) predicting, based upon magnitude of dilations in vein diameter, whether deep vein thrombosis will occur.

2. The procedure according to claim 1 wherein immobilizing the part of the subject includes the steps of:
   providing an impression casting for immobilizing the part; and securing the impression casting on a support table.

3. A procedure for predicting the occurence of deep vein thrombosis in a subject:
   monitoring changes in a vein's diameter over time while the subject is undergoing a surgical procedure; and
   predicting, based upon the magnitude of the changes, whether deep vein thrombosis will occur throughout the subject.

* * * * *